(12) United States Patent
Moore

(10) Patent No.: US 10,226,490 B2
(45) Date of Patent: *Mar. 12, 2019

(54) PROBIOTIC COMPOSITIONS AND METHODS FOR INDUCING AND SUPPORTING WEIGHT LOSS

(71) Applicant: Brenda E. Moore, Springfield, OH (US)

(72) Inventor: Brenda E. Moore, Springfield, OH (US)

(*) Notice: Subject to any disclaimer, the term of this patent is extended or adjusted under 35 U.S.C. 154(b) by 68 days.

This patent is subject to a terminal disclaimer.

(21) Appl. No.: 15/185,942

(22) Filed: Jun. 17, 2016

(65) Prior Publication Data

US 2016/0310545 A1 Oct. 27, 2016

Related U.S. Application Data

(63) Continuation of application No. 12/255,152, filed on Oct. 21, 2008, now Pat. No. 9,371,510.

(60) Provisional application No. 60/982,844, filed on Oct. 26, 2007.

(51) Int. Cl.
*C12N 1/20* (2006.01)
*A61K 35/741* (2015.01)

(52) U.S. Cl.
CPC ............ *A61K 35/741* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 9,371,510 B2* | 6/2016 | Moore | A61K 35/741 |
| 2003/0133875 A1* | 7/2003 | Kelly | A61K 31/02 424/9.2 |
| 2004/0028689 A1 | 2/2004 | Borody | |
| 2004/0115177 A1 | 6/2004 | Harris et al. | |
| 2005/0180962 A1* | 8/2005 | Raz | A61K 9/0095 424/93.45 |
| 2007/0218164 A1 | 9/2007 | Stojanovic | |

FOREIGN PATENT DOCUMENTS

| | | |
|---|---|---|
| EP | 0433299 | 5/1998 |
| WO | 96/08261 A1 | 3/1996 |
| WO | 96/11014 A1 | 4/1996 |
| WO | 99/19459 A1 | 4/1999 |
| WO | 03/046580 A1 | 6/2003 |
| WO | 2005/060937 A1 | 7/2005 |
| WO | WO 2006-102350 * | 9/2006 |
| WO | 2008/076696 A2 | 6/2008 |

OTHER PUBLICATIONS

Ley et al. (Microbial ecology: Human gut microbes associated with obesity., Nature 2006, 444: 1022-1023).*
Prakash et al. Practice and prospects of microbial preservation, FEMS Microbiology Letters, (2013), 339: 1-9).*
Cited in Opposition of EP 2211879; Backhed, F. et al.; "The gut microbiota as an environmental factor that regulates fat storage"; PNAS, vol. 101, No. 44, pp. 15718-15723; Nov. 2, 2004.
Cited in Opposition of EP 2211879; Ley, R. E. et al.; Microbial Ecology, "Human Gut Microbes Associated with Obesity"; Nature, vol. 444; Dec. 28, 2006.
Cited in Opposition of EP 2211879; Food and Agriculture Organization of the United Nations and the World Health Organization; "Guidelines for the Evaluation of Probiotics in Food"; London and Ontario, Canada; Apr. 30, 2002 and May 1, 2002.
Cited in Opposition of EP 2211879; Tortora, G. J. et al.; "*Escherichia coli* Gastroenteritis"; Microbiology an Introduction, Eighth Edition; Pearson Cummings; 2003.
Cited in Opposition of EP 2211879; National Academy of Sciences; "Guidelines for the Care and use of Mammals in Neuroscience and Behavioral Research"; 2003.
Cited in Opposition of EP 2211879; Dell, R. B. et al.; "Sample Size Determination"; National Institute of Health; NIH Public Access, Author Manuscript; Ilar J. Author manuscript, published in final edited form as: Ilar J. 2002; 43 (4), pp. 207-213; 2002.
Cited in Opposition of EP 2211879; Devore, J. et al.; "Statistics—The Exploration and Analysis of Data"; West Publishing Company; 1986.
Cited in Opposition of EP 2211879; National institute of Health; "What Investigators Need to Know About the Use of Animals—Proper use of animals, including the avoidance or minimization of discomfort, distress, and pain when consistent with sound scientific practices, is imperative"; NIH Publication No. 06-6009; 2006.
Cited in Opposition of EP 2211879; Mazmanian, S. K. et al.; "An Immunomodulatory Molecule of Symbiotic Bacteria Directs Maturation of the Host Immune System"; Cell, vol. 122, pp. 107-118; Jul. 15, 2005.
Cited in Opposition of EP 2211879; Frick, J. S. et al.; "Identification of Commensal Bacterial Strains That Modulate Yersinia enterocolitica and Dextran Sodium Sulfate-Induced Inflammatory Responses: Implications for the Development of Probiotics"; Infection and Immunity, vol. 75, No. 7, pp. 3490-3497; Jul. 2007.
Cited in Opposition of EP 2211879; Pierce, B. A.; "Genetics a Conceptual Approach", Second Edition; W.H. Freeman and Company, New York; 2005.
Cited in Opposition of EP 2211879; Wu, Q. et al.; "Comparative DNA Sequence Analysis of Mouse and Human Protocadherin Gene Clusters"; Genome Research; 2001.
Cited in Opposition of EP 2211879; Leser, T. D. et al.; "Changes in Bacterial Community Structure in the Colon of Pigs Fed Different Experimental Diets and after Infection with Brachyspira hyodysenteriae", Applied and Environmental Vlicrobiology, vol. 66, No. 8, pp. 3290-3296; American Society for Microbiology; Aug. 2000.
Cited in Opposition of EP 2211879; Gibson, G. R. et al.; "Dietary Modulation of the Human Colonic Microbiota: Introducing the Concept of Prebiotics"; American Institute of Nutrition, pp. 1401-1412; 1995.

(Continued)

*Primary Examiner* — Iqbal H Chowdhury
(74) *Attorney, Agent, or Firm* — Thomas E. Lees, LLC

(57) ABSTRACT

A probiotic composition for inducing or supporting weight loss in a subject, the probiotic composition including an effective amount of a bacteria selected from the genus *Bacteroides* and a carrier for delivering the bacteria to the subject.

20 Claims, No Drawings

(56) References Cited

OTHER PUBLICATIONS

Cited in Opposition of EP 2211879; Hyde, D. R.; Introduction to Genetic Principles; McGraw-Hill Higher Education; Chapter 16, p. 525; 2009.
Cited in Opposition of EP 2211879; Tortora, G. J. et al.; "Classification of Organisms"; Microbiology an Introduction, Ninth Edition; Pearson Cummings; 2006.
Cited in Opposition of EP 2211879; Sigma-Aldrich Corporation; Material Safety Data Sheet, Version 3.4; Feb. 21, 2014.
Cited in Opposition of EP 2211879; U.S. Department of Health and Human Services, Food and Drug Administration, and Center for Biologics Evaluation and Research; Guidance for Industry, "Early Clinical Trials with Live Biotherapeutic Products: Chemistry, Manufacturing, and Control Information"; Feb. 2012.
Cited in Opposition of EP 2211879; Williams, M. H.; Nutrition for Health, Fitness, Sport, Eighth Edition; McGraw-Hill Higher Education; 2007.
Cited in Opposition of EP 2211879; Rodin, J. et al.; "Weight Cycling and Fat Distribution"; International Journal of Obesity, pp. 303-310; 1990.
Cited in Opposition of EP 2211879; Grosvenor, M. B. et al.; Nutrition Everyday Choices; John Wiley & Sons, Inc.; 2006.
Cited in Opposition of EP 2211879; Ley, R. E. et al.; "Obesity Alters Gut Microbial Ecology"; PNAS, vol. 102, No. 31; Aug. 2, 2005.
Cited in Opposition of EP 2211879; Ludwig, W. et al.; "Revised Road Map to the Phylum Firmicutes"; Bergey's Manual of Systematic Bacteriology, Second Edition; Springer; 2009.
Cited in Opposition of EP 2211879; Kreig, N. R. et al.: Bergey's Manual of Systematic Bacteriology, Second Edition, vol. Four, "The Bacteroidetes, Spirochaetes, Tenericutes (Mollicutes), Acidobacteria, Fibrobacteres, Fusobacteria, Dictyoglomi, Gemmatimonadetes, Lentisphaerae, Verrucomicrobia, Chlamydiae, and Planctomycetes"; Springer; 2010.
Cited in Opposition of EP 2211879; Macfarlane G. T. et al.; "The Colonic Flora, Fermentation, and Large Bowel Digestive Function"; The Large Intestine: Physiology, Pathophysiology, and Disease; pp. 51-92; Raven Press, New York; 1991.
Cited in Opposition of EP 2211879; Cummings, J. H.; Gut; "Short chain fatty acids in the human colon"; vol. 22, pp. 763-779; 1981.
European Patent Office; Reply to Statement of Grounds of Appeal submitted by Opponent for Patent Application No. 08841594.8—European Patent No. 2211879; Feb. 16, 2017.
Cited in Opposition of EP 2211879; Zirkin et al.; "Testicular Steroidogenesis in the Aging Brown Norway Rat"; Journal of Andrology, vol. 14, No. 2, pp. 118-123; Mar./Apr. 1993.
Cited in Opposition of EP 2211879; "Basic Concepts of t Distribution"; Real Statistics Using Excel; http://www.real-statistics.com/students-t-distribution/t-distribution-basic-concepts/; Jun. 5, 2016 (dated located through https://web.archive.org/web/20160608232416/http://www.real-statistics.com:80/students-t-distribution/t-distribution-basic-concepts/).
Australian Government; IP Australia; Patent Examination Report No. 1 for Australian Patent Application No. 2008317000; Feb. 15, 2013.
Canadian Patent Office; Examination Search Report for Canadian Patent Application No. 2,740,434; Nov. 25, 2014.
Cited in Opposition of EP 2211879; Salyers, A. A. et al.; "Digestion of Larch Arabinogalactan by a Strain of Human Colonic Bacteroides Growing in Continuous Culture"; J. Agric. Food Chem., pp. 475-480; American Chemical Society; 1981.
Cited in Opposition of EP 2211879; Ludwig, W. et al; Molecular Phylogeny of Bacteria Based on Comparative Sequence Analysis of Conserved Genes; Microbial Phylogeny and Evolution Concepts and Controversies (edited by Jan Sapp); Oxford University Press; 2005.
Cited in Opposition of EP 2211879; Vael, C. et al.; "Intestinal Microflora and Body Mass Index During the First Three Years of Life: An Observational Study"; Gut Pathogens; 2011.
Cited in Opposition of EP 2211879; Collado, M. et al.; "Distinct composition of gut microbiota during pregnancy in overweight and normal-weight women"; The American Journal of Clinical Nutrition, No. 88, pp. 894-899; 2008.
European Patent Office; Annex to Written Opinion for European Patent Application No. 08841594.8; dated Jun. 18, 2013.
European Patent Office; Summary of Facts and Submissions for European Patent Application No. 08841594.8—European Patent No. 2211879; Aug. 17, 2015.
European Patent Office; Annex to Communication relating to Oral Proceedings for European Patent Application No. 38841594.8—European Patent No. 2211879; Jun. 14, 2016.
European Patent Office; Decision Revoking the European Patent for European Patent Application No. 08841594.8—European Patent No. 2211879; Jun. 14, 2016.
European Patent Office; Summary of Facts and Submissions for European Patent Application No. 08841594.8—European Patent No. 2211879; Jun. 14, 2016.
European Patent Office; Notice of Opposition to a European Patent for European Patent Application No. 08841594.8—European Patent No. 2211879; dated Feb. 5, 2015.
European Patent Office; Provision of the minutes for European Patent Application No. 08841594.8—European Patent No. 2211879; Jun. 14, 2016.
European Patent Office; International Preliminary Report on Patentability and Written Opinion of the International Searching Authority for International Application No. PCT/US2008/080601; Apr. 27, 2010.
D Young & Co LLP; Written Submission to European Patent Office for European Patent Application No. 08841594.8—European Patent No. 2211879; Feb. 19, 2016.

* cited by examiner

PROBIOTIC COMPOSITIONS AND METHODS FOR INDUCING AND SUPPORTING WEIGHT LOSS

CROSS-REFERENCE TO RELATED APPLICATIONS

This application is a continuation of U.S. patent application Ser. No. 12/255,152, filed Oct. 21, 2008, now allowed, entitled PROBIOTIC COMPOSITIONS AND METHODS FOR INDUCING AND SUPPORTING WEIGHT LOSS, which claims the benefit of U.S. Provisional Patent Application Ser. No. 60/982,844, filed Oct. 26, 2007, the disclosures of which are hereby incorporated herein by reference.

BACKGROUND

The present patent application is directed to probiotic compositions and, more particularly, to compositions formulated with *Bacteroides* bacteria for administration to humans or other animals for inducing and supporting weight loss therein.

The typical American diet can be classified as anything but healthy. According to the ARS Food Survey Group, 50% of Americans eat only one serving of whole grains per day, 59% do not eat enough vegetables and 76% do not meet daily fruit recommendations (Cleveland, L. E., et al., Pyramid Servings Data, ARS Food Survey Research Group.) Over 80% of American women do not consume enough dairy, while the intake of meats, fats and sweets greatly exceed recommendations. These eating habits result in a deficiency of nutrients and contribute to the rising incidence of health problems experienced by younger and younger members of the population (Kranz, S. et. al., Dietary fiber intake by American preschoolers is associated with more nutrient-dense foods; *J. Amer. Diet. Assoc.* 105:221, 2005; Lytle, L., Nutritional issues for adolescents, *J. Amer. Diet. Assoc.* 102:58, 2002). In addition, poor food choices have increased the incidence of obesity to 31%, and more than 64% of American adults are considered to be overweight. The problem doesn't stop there. The percentage of young children and adolescents who are overweight or obese has been steadily increasing since 1991 (Kopkin, J. P. et. al., Preventing childhood obesity: Health in the balance-Executive Summary, *J. Amer. Diet. Assoc.* 105:131, 2005).

Health problems related to weight are now second only to tobacco use as the leading of cause of preventable deaths (Mokdad, A. H., et. al., Actual causes of death in the Unites States, *JAMA* 291:1238, 2004). It is estimated that preventable weight-related illness costs the nation approximately $99.2 billion every year and that this cost is more than the cost estimated for tobacco and alcohol use combined. (National Institutes of Diabetes and Digestive and Kidney Diseases, Weight Control Information Network. *Statistics Related to Overweight and Obesity*.) When unhealthy, highly processed foods are consumed regularly, nutrient deficiencies result, increasing the incidence of health problems such as heart disease, high blood pressure and type 2 diabetes (Cordain, L. et. al., Origins and evolution of the Western diet: health implications for the 21st century. *Amer. J. Clin. Nutr.* 81: 342, 2005).

While the obesity epidemic has risen rapidly in the last three decades, it cannot be accounted for by changes within the human gene pool. However, the trillions of prokaryotic bacteria that reside within the human gastrointestinal tract constitute a much larger genetic pool than that which can be found in the eukaryotic cells that constitute the human body (Bajzer, M. and R. J. Seeley, Obesity and gut flora. *Nature.* 444:1009, 2006). While the human genome takes generations to change, genetic contributions by changing populations of bacterial cells require mere days. It has been noted that the obesity epidemic has certain characteristics indicative of an infectious nature (Bray, G. A. et al., Beyond energy balance: There is more to obesity than kilocalories. *J. Amer. Diet. Assoc.* 105:S17, 2005). These bacterial populations, and subsequently their contribution to the physiological functioning of the eukaryotic cells, can change very quickly and could account for the infectious characteristic of the epidemic.

It has been recognized for some time that the human gut is the largest immune organ in the body, containing 65% of the immune tissue overall and contributing up to 80% of the immunoglobulin-producing tissue (Benmark, S., Gut microenvironment and immune function. *Curr. Opin. Clin. Nutrit. Meta. Care.* 2:1, 1999; Brandzaeg, P. et. al., Immunology and immunopathology of the human gut mucosa, humoral immunity and intraepithelial lymphocytes. *Gastroenterology,* 97:1562, 1989). In addition, several authors have noted that bacteria play a significant role in genetic expression within the eukaryotic cells of the human body (Muzmanian, S. K., et. al., An immunomodulatory molecule of symbiotic bacteria directs maturation of the host immune system. *Cell* 122:107, 2005; Rath, H. C. et. al., Normal luminal bacteria, especially *Bacteroides* species, mediate chronic colitis, gastritis and arthritis in HLA-B27/Human beta-2 microglobin transgenic rats. *J. Clin. Invest.* 89:945, 1996; Lopez-Barado, Y. S. et. al., Bacterial exposure induces and activates matrilysin in mucosal epithelial cells. *J. Cell. Biol.* 148(6):1305, 2000; Wang, Q. et. al., A bacterial carbohydrate links innate and adaptive responses through Toll-like receptor-2. *J. Exp. Med.* 203(13):2853, 2006; Frick, J. S., et. al., Identification of commensal bacterial strains that modulate *Yersinia enterocolitica* and dextran sodium sulfate-induced inflammatory responses: Implications for the development of probiotics. *Infect. Immun.* 75(7):3490, 2007; Kim, J. M., et. al., Nuclear factor-kappa B activation pathway in intestinal epithelial cells is a major gene expression and neutrophil migration induced by *Bacteroides fragilis* endotoxin. *Clin. Exp. Immunol.* 130:59, 2002). These data support the role that bacterial populations play in the physiological function of genetic expression within the eukaryotic cells of the human host, perhaps providing a key to stemming the obesity epidemic.

There have been many animal research studies that have utilized germ-free animals as well as animals that have established microbial populations. In 1993, results of a study were published on the effect of protozoa on metabolism and concentrations of bacteria and fungi in the hind gut of the Shetland pony (Moore and Dehority, *J. Anim. Sci.,* 71:3350). These animals were fistulated in both the cecum and the colon to allow easy access to the contents of the gastrointestinal tract for research purposes. Defaunation (i.e., removing a segment of the established microbial populations of an animal) was also outlined in this publication. Defaunation followed by establishment of rumen protozoa from a fistulated sheep was then accomplished (Moore, unpublished data).

Procedures utilized in these trials to remove debris and much of the microbial populations from the equine hind gut are remarkably similar to the safe and effective procedures currently used by the medical community to prepare patients for a colonoscopy. It is therefore hypothesized that microbial populations in the human gastrointestinal tract could be changed by utilizing these procedures, followed by inoculation with a probiotic to establish friendly populations of bacteria more conducive to weight loss.

In 2006, researchers reported that microbiota containing higher concentrations of the *Bacteroidetes* bacteria obtained from the gut of a "lean" mouse were inoculated into germ-free mice, resulting in the subject mice having significantly less body fat than when "obese microbiota" containing differing microorganisms were used for inoculation (Turnbaugh et. al., An obesity-associated gut microbiome with increased capacity for energy harvest, *Nature*, 444:1027). These results indicate that the bacterial populations colonizing the human subject may play a role in the harvesting of energy from the host's diet.

Several scientists at the Stanford University School of Medicine reported similar findings in human subjects. Forty-two patients who had successfully undergone bariatric surgery were placed into one of two groups, a treatment group receiving 2.4 billion live colony forming units of *Lactobacillus* bacteria per day or a control group which received a placebo. After six months, the treatment group had lost 4% more weight than the control group and had higher Gastrointestinal Related Quality of Life Scores than the placebo group (Woodad, G. A., et. al., Probiotics improve weight loss, GI-related quality of life and H2 breath tests after gastric bypass surgery: A prospective, randomized trial. *Digestive Disease Week Conference*, Abstract #343, May 19, 2008, San Diego, Calif.). *Lactobacillus* cultures have seldom been indicated for weight loss.

Accordingly, it is hypothesized that successful gastrointestinal establishment of a probiotics culture specifically formulated and scientifically demonstrated to decrease weight gain, such as *Bacteroides* cultures (as is discussed below), may significantly improve weight loss in persons identified as overweight or obese and may help prevent weight gain in those who are already lean.

BRIEF SUMMARY

In one aspect, the disclosed probiotic composition may include a bacteria selected from the genus *Bacteroides* and a pharmaceutically acceptable carrier.

In another aspect, the disclosed probiotic composition may be formulated for inducing or supporting weight loss in a subject, wherein the probiotic composition may include a safe and effective amount of a bacteria selected from the genus *Bacteroides* and a carrier for delivering the bacteria to the subject.

In another aspect, the disclosed method for inducing weight loss in a human subject may include the steps of cleansing a gastrointestinal tract of the human subject and, after the cleansing step, introducing a population of *Bacteroides* bacteria into the gastrointestinal tract of the human subject.

Other aspects of the disclosed probiotic and method for inducing and supporting weight loss will become apparent from the following detailed description and the appended claims.

DETAILED DESCRIPTION

The present disclosure provides a probiotic composition including an appropriate quantity of bacteria from the genus *Bacteroides*, as well as a system and method for using the disclosed probiotic composition to induce and sustain weight loss in animals, such as humans, horses, rats, mice, ruminants, primates, monkeys, hamsters, rabbits, cats and various avian and fish species. The disclosed probiotic composition may be administered to a subject to increase the population of appropriate *Bacteroides* bacteria in the gastrointestinal tract of the host. It is believed that successful establishment and propagation of appropriate *Bacteroides* bacteria in the gastrointestinal tract of a subject may induce and/or support beneficial weight loss, particularly in humans.

The *Bacteroides* bacteria may be received in a carrier to facilitate delivery to a subject animal in need thereof. As used herein, the term "carrier" is intended to broadly refer to any substance (e.g., a tableting agent or a liquid) or article (e.g., a capsule shell or a polymer matrix) that facilitates administration of the *Bacteroides* bacteria by providing a medium for their conveyance to the consuming animal. Those skilled in the art will appreciate that the carrier should be substantially non-toxic in the amounts employed and should not significantly inhibit the intended probiotic value of the *Bacteroides* bacteria in the composition.

Bacteria useful in the disclosed probiotic composition include, but are not limited to *Bacteroides thetaiotaomicron* (ATTC29148), *B. fragilis* (NCTC9343), *B. vulgatus* (ATCC8482), *B. distasonis* (ATCC8503), *B. ovatus, B. adolescentis, B. stercoris, B. merdae, B. uniformis, B. eggerithii,* and *B. caccae* with *B. fragilis* as the type strain. However, according to one aspect, those skilled in the art will appreciate that any bacteria from the genus *Bacteroides* that induces, promotes, sustains, encourages, or is otherwise associated with weight loss when established in the gastrointestinal tract of the subject may be used in the disclosed probiotic composition without departing from the scope of the present disclosure. In another aspect, any bacteria of the genus *Bacteroides* may be used, regardless of whether or not the bacteria has been genetically modified, engineered, or altered in any way.

The *Bacteroides* bacteria useful in the disclosed probiotic composition may be provided as a live culture, as a dormant material or a combination thereof. Those skilled in the art will appreciate that the *Bacteroides* bacteria may be rendered dormant by, for example, a lyophilization process, as is well known to those skilled in the art.

An example of an appropriate lyophilization process may begin with a media carrying appropriate *Bacteroides* bacteria to which an appropriate protectant may be added for cell protection prior to lyophilization. Examples of appropriate protectants include, but are not limited to, distilled water, polyethylene glycol, sucrose, trehalose, skim milk, xylose, hemicellulose, pectin, amylose, amylopectin, xylan, arabinogalactan, starch (e.g., potato starch or rice starch) and polyvinylpyrrolidone. Gasses useful for the lyophilization process include but are not limited to nitrogen and carbon dioxide.

In one aspect, the *Bacteroides* bacteria in the disclosed probiotic composition may be provided as a dispersion in a solution or media. In another aspect, the *Bacteroides* bacteria in the disclosed probiotic may be provided as a semi-solid or cake. In another aspect, the *Bacteroides* bacteria in the disclosed probiotic may be provided in powdered form.

Quantities of appropriate *Bacteroides* bacteria may be generated using a fermentation process. For example, a sterile, anaerobic fermentor may be charged with media, such as glucose, polysaccharides, oligosaccharides, mono- and disaccharides, yeast extract, protein/nitrogen sources, macronutrients and trace nutrients (vitamins and minerals), and cultures of the desired *Bacteroides* bacteria may be added to the media. During fermentation, concentration (colony forming units per gram), purity, safety and lack of contaminants may be monitored to ensure a quality end result. After fermentation, the *Bacteroides* bacteria cells may be separated from the media using various well known techniques, such as filtering, centrifuging and the like. The separated cells may be dried by, for example, lyophilization, spray drying, heat drying or combinations thereof, with protective solutions/media added as needed.

The disclosed probiotic compositions may be prepared in various forms, such as capsules, suppositories, tablets, food/drink and the like. Optionally, the disclosed probiotic compositions may include various pharmaceutically acceptable excipients, such as microcrystalline cellulose, mannitol, glucose, defatted milk powder, polyvinylpyrrolidone, starch and combinations thereof.

In one aspect, the disclosed probiotic composition may be prepared as a capsule. The capsule (i.e., the carrier) may be a hollow, generally cylindrical capsule formed from various substances, such as gelatin, cellulose, carbohydrate or the like. The capsule may receive the *Bacteroides* bacteria therein. Optionally, and in addition to the appropriate *Bacteroides* bacteria, the capsule may include but is not limited to coloring, flavoring, rice or other starch, glycerin, caramel color and/or titanium dioxide.

In a second aspect, the disclosed probiotic composition may be prepared as a suppository. The suppository may include but is not limited to the appropriate *Bacteroides* bacteria and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax and coloring agents.

In a third aspect, the disclosed probiotic may be prepared as a tablet. The tablet may include the appropriate *Bacteroides* bacteria and one or more tableting agents (i.e., carriers), such as dibasic calcium phosphate, stearic acid, croscarmellose, silica, cellulose and cellulose coating. The tablets may be formed using a direct compression process, though those skilled in the art will appreciate that various techniques may be used to form the tablets.

In a fourth aspect, the disclosed probiotic may be formed as food or drink or, alternatively, as an additive to food or drink, wherein an appropriate quantity of *Bacteroides* bacteria is added to the food or drink to render the food or drink the carrier.

The concentration of the *Bacteroides* bacteria in the disclosed probiotic composition may vary depending upon the desired result, the type of bacteria used, the form and method of administration, among other things. For example, a probiotic composition may be prepared having a count of *Bacteroides* bacteria in the preparation of no less than about $1 \times 10^6$ colony forming units per gram, based upon the total weight of the preparation.

Specific examples of probiotic compositions contemplated by the present disclosure are provided below.

EXAMPLE 1

Capsule

Using a lyophilization process, a quantity of *B. thetaiotaomicron* cells was prepared in powdered form ("Active Ingredient 1").

TABLE 1

| No. | Ingredient | mg/Capsule |
| --- | --- | --- |
| 1 | Active Ingredient 1 | 200 |
| 2 | Lactose USP | 180 |
| 3 | Corn Starch, Food Grade | 60 |
| 4 | Magnesium Stearate NF | 10 |

Item numbers 1-4 from Table 1 were mixed in a suitable mixer for 10 minutes. After mixing, 450 milligrams of the mixture was charged into a two-piece gelatine capsule and the capsule was sealed.

EXAMPLE 2

Tablet

Using a lyophilization process, a quantity of *B. uniformis* cells was prepared in powdered form ("Active Ingredient 2").

TABLE 2

| No. | Ingredient | mg/Tablet |
| --- | --- | --- |
| 1 | Active Ingredient 2 | 65 |
| 2 | Microcrystalline Cellulose | 135 |
| 3 | Glucose | 250 |

Item numbers 1-3 from Table 2 were mixed in a suitable mixer for 10 minutes. The mixture was then compressed into 450 milligram tablets using a tableting press.

EXAMPLE 3

Suppository

Using a lyophilization process, a quantity of *B. vulgatus* cells was prepared in powdered form ("Active Ingredient 3")

TABLE 3

| No. | Ingredient | g/dosage |
| --- | --- | --- |
| 1 | Active Ingredient 3 | 15 |
| 2 | Cacao Butter | 30 |
| 3 | Yellow Wax | 5 |
| 4 | Petroleum Jelly | 5 |
| 5 | Sodium Stearate | 3 |

Item numbers 2-4 from Table 3 were charged into a suitable mixer and heated to a temperature of 60° C. while constantly stirring to form Mixture 1. Separately, item numbers 1 and 5 from Table 9 were charged into a mixer and mixed for 10 minutes to form Mixture 2. Slowly, and while stirring, Mixture 2 was added to Mixture 1 to form Mixture 3. Mixture 3 was continuously stirred for 10 minutes and then poured into pre-formed suppository shells. The filled suppository shells were allowed to cool until the suppositories set.

The disclosed probiotic compositions may be administered to a subject to induce weight loss pursuant to an appropriate cleansing and inoculation protocol. Furthermore, the disclosed probiotic compositions may be used to sustain weight loss in the subject pursuant to an appropriate inoculation and maintenance protocol.

In particular, it may be desirable to cleanse the gastrointestinal tract of the user prior to administration of the disclosed probiotic compositions. An appropriate cleansing procedure may include a cleansing diet coupled with, or followed by, administration of a chemical/solution/powder etc. to remove debris from the gut. The cleansing procedure may continue for about 18 hours (e.g., beginning in the morning) and may continue until generally full debris removal from the gastrointestinal tract has been achieved.

The cleansing diet may include bouillon or broth, water (preferably) or liquid generally without sugar or caffeine, plain weak coffee or tea, fruit juice (no pulp or added sugar), gelatin or popsicles. However, those skilled in the art will appreciate that other foods and beverages may be consumed during cleansing.

Furthermore, those skilled in the art will appreciate that any medically approved chemical/solution that induces diarrhea may be used as the cleansing chemical/solution. Examples of appropriate cleansing chemicals/solutions include, without limitation, magnesium citrate, sodium phosphate, dibasic (any form), sodium phosphate, monobasic, any form, potassium phosphate, monobasic, any form, and potassium phosphate, dibasic, any form.

After the gastrointestinal tract has been cleansed, inoculation of the *Bacteroides* bacteria may begin with the administration of the disclosed probiotic compositions. An appropriate probiotic composition administration schedule may include, for example, administration of a certain number of probiotic compositions (e.g., 3 capsules) with each meal for a certain number of days (e.g., for three days). However, those skilled in the art will appreciate that the quantity and frequency of administration of the disclosed probiotic compositions may depend upon the type of bacteria being administered, the concentration of bacteria in the preparation, the weight, height and/or age of the subject, among other things.

Weight loss may be sustained by continued administration of the disclosed probiotic compositions (e.g., one capsule per day or one capsule with each meal) together with a proper maintenance program, including diet and exercise. For example, a subject may be advised to avoid foods that are high in fat and sugar and focus on consuming a certain quantity of fruits and vegetables (e.g., two fresh fruits and two vegetables every day which support the probiotic as well as the host). Furthermore, a subject may be advised to undergo a minimum three sessions of 30 minutes of moderate exercise, such as brisk walking, each week. More fresh fruits and vegetables and more exercise should be encouraged.

To encourage proper use of the disclosed probiotic compositions, the compositions may be provided together with instructions for use, suggested cleansing/inoculation and inoculation/maintenance protocols, and/or a covenant that a user may customize and use to track progress. The instructions and/or covenant may be provided together with the disclosed probiotic compositions in a kit or bundle.

Accordingly, at this point, those skilled in the art will appreciate that the disclosed probiotic compositions and associated methods may be used to aid weight loss without the need for invasive surgeries or other drastic techniques by increasing the populations of beneficial bacterial species in the gastrointestinal tract. The beneficial bacteria may be sustained with continued administration of the probiotic composition and, optionally, an appropriate maintenance regimen, including proper diet and exercise.

Although various aspects of the disclosed probiotic compositions and methods for inducing and supporting weight loss have been shown and described, modifications may occur to those skilled in the art upon reading the specification. The present application includes such modifications and is limited only by the scope of the claims.

What is claimed is:

1. A probiotic composition for inducing or supporting weight loss, or preventing or reducing weight gain in a subject, the probiotic composition comprising:
   lyophilized probiotic bacteria that consists of bacteria selected from the genus *Bacteroides*, wherein:
      the lyophilized probiotic bacteria is separated from a media carrying *Bacteroides* to which a first protectant is added for cell protection prior to lyophilization such that the probiotic bacteria is rendered dormant by lyophilization; and
   a carrier that comprises at least one pharmaceutically acceptable excipient that is mixed with the lyophilized probiotic bacteria in a pharmaceutically effective amount and acts as a second protectant that cooperates together with the first protectant to protect and preserve the genus *Bacteroides* bacteria until delivery of the genus *Bacteroides* bacteria into the gastrointestinal tract of a subject to establish and propagate the genus *Bacteroides* bacteria and thereby to increase the populations of beneficial bacterial species in the gastrointestinal tract to induce or support weight loss, or prevent or reduce weight gain in the subject.

2. The probiotic composition according to claim 1, wherein the genus *Bacteroides* bacteria is selected from the group consisting of *Bacteroides thetaiotaomicron, B. fragilis, B. vulgatus, B. distasonis, B. ovatus, B. stercoris, B. merda, B. uniformis, B. eggerithii*, and *B. caccae*.

3. The probiotic composition according to claim 1, wherein the carrier is implemented as an article in the form of a capsule shell or a polymer matrix.

4. The probiotic composition according to claim 1, wherein the carrier is implemented as a select one of a liquid substance or a tableting agent.

5. The probiotic composition according to claim 1, wherein the at least one pharmaceutically acceptable excipient is selected from the group consisting of microcrystalline cellulose, mannitol, glucose, defatted milk powder, polyvinylpyrrolidone, and starch.

6. The probiotic composition according to claim 1, wherein the first protectant is selected from the group consisting of distilled water, polyethylene glycol, sucrose, trehalose, skim milk, xylose, hemicellulose, pectin, amylose, amylopectin, xylan, arabinogalactan, starch, and polyvinylpyrrolidone.

7. The probiotic composition according to claim 6, wherein the at least one pharmaceutically acceptable excipient that acts as the second protectant is selected from the group consisting of microcrystalline cellulose, mannitol, glucose, defatted milk powder, polyvinylpyrrolidone, and starch.

8. The probiotic composition according to claim 1, wherein the genus *Bacteroides* has a count of at least 1,000,000 colony forming units per gram, based upon a total weight of the probiotic composition.

9. The probiotic composition according to claim 1, wherein the probiotic composition provides the bacteria selected from the genus *Bacteroides* as a select one of:
   a dispersion in a solution;
   a dispersion in a media;
   a semi-solid;
   a cake; or
   a powdered form.

10. The probiotic composition according to claim 1, wherein the carrier is implemented as a hollow capsule comprising at least one of gelatin, cellulose, carbohydrate, coloring, flavoring, starch, glycerin, caramel color, and titanium dioxide.

11. The probiotic composition according to claim 1, wherein the carrier is implemented as a suppository comprising at least one of polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax, and a coloring agent.

12. The probiotic composition according to claim 1, wherein the carrier is implemented as a tablet comprising at least one of dibasic calcium phosphate, stearic acid, croscarmellose, silica, cellulose, and cellulose coating.

13. The probiotic composition according to claim 1, wherein the carrier is implemented as a select one of a food, a food additive, a drink, and a drink additive.

14. A method of producing a probiotic composition for inducing or supporting weight loss, or preventing or reducing weight gain in a subject, the probiotic composition comprising:
providing lyophilized probiotic bacteria that consists of bacteria selected from the genus *Bacteroides*, wherein:
the lyophilized probiotic bacteria is separated from a media carrying *Bacteroides* to which a first protectant is added for cell protection prior to lyophilization such that the probiotic bacteria is rendered dormant by lyophilization;
and
providing a carrier that comprises at least one pharmaceutically acceptable excipient that is mixed with the lyophilized probiotic bacteria in a pharmaceutically effective amount and acts as a second protectant that cooperates together with the first protectant to protect and preserve the genus *Bacteroides* bacteria until delivery of the genus *Bacteroides* bacteria into the gastrointestinal tract of a subject to establish and propagate the genus *Bacteroides* bacteria and thereby to increase the populations of beneficial bacterial species in the gastrointestinal tract to induce or support weight loss, or prevent or reduce weight gain in the subject.

15. The method according to claim 14, wherein providing lyophilized probiotic bacteria that consists of bacteria selected from the genus *Bacteroides*, comprises selecting the genus *Bacteroides* bacteria from the group consisting of *Bacteroides* thetaiotaomicron, *B. fragilis, B. vulgatus, B. distasonis, B. ovatus, B. stercoris, B. merda, B. uniformis, B. eggerithii,* and *B. caccae.*

16. The method according to claim 14, wherein providing lyophilized probiotic bacteria further comprises providing a pharmaceutically acceptable carrier with the composition, where the pharmaceutically acceptable carrier is implemented as an article in the form of a select one of a capsule, a polymer matrix, a liquid or a tablet.

17. The method according to claim 14, wherein providing a carrier that comprises at least one pharmaceutically acceptable excipient comprises providing the at least one pharmaceutically acceptable excipient selected from the group consisting of microcrystalline cellulose, mannitol, glucose, defatted milk powder, polyvinylpyrrolidone, and starch.

18. The method according to claim 14, further comprising:
generating quantities of *Bacteroides* bacteria using a sterile, anaerobic fermentor charged with media and cultures of *Bacteroides,*
wherein:
a first protectant is added for cell protection prior to lyophilization by adding the first protectant selected from the group consisting of distilled water, polyethylene glycol, sucrose, trehalose, skim milk, xylose, hemicellulose, pectin, amylose, amylopectin, xylan, arabinogalactan, starch, and polyvinylpyrrolidone.

19. The method according to claim 18, wherein providing at least one pharmaceutically acceptable excipient comprises providing the at least one pharmaceutically acceptable excipient selected from the group consisting of microcrystalline cellulose, mannitol, glucose, defatted milk powder, polyvinylpyrrolidone, and starch.

20. The method according to claim 14, further comprising providing the genus *Bacteroides* in a count of at least 1,000,000 colony forming units per gram, based upon a total weight of the probiotic composition.

* * * * *